(12) United States Patent
    Galperin

(10) Patent No.: US 9,750,601 B2
(45) Date of Patent: Sep. 5, 2017

(54) METHOD AND APPARATUS FOR ENDOTHELIAL KERATOPLASTY

(71) Applicant: E.K.-D.D.S. LTD., Zoran (IL)

(72) Inventor: Natan Galperin, Zoran (IL)

(73) Assignee: E.K.-D.D.S. LTD., Tel Aviv (IL)

( * ) Notice: Subject to any disclaimer, the term of this patent is extended or adjusted under 35 U.S.C. 154(b) by 171 days.

(21) Appl. No.: 14/430,978

(22) PCT Filed: Sep. 12, 2013

(86) PCT No.: PCT/IL2013/050773
    § 371 (c)(1),
    (2) Date: Mar. 25, 2015

(87) PCT Pub. No.: WO2014/049591
    PCT Pub. Date: Apr. 3, 2014

(65) Prior Publication Data
    US 2015/0238307 A1    Aug. 27, 2015

(30) Foreign Application Priority Data

Sep. 27, 2012   (IL) .......................................... 222183

(51) Int. Cl.
    *A61B 18/08*   (2006.01)
    *A61F 2/14*    (2006.01)
    *A61F 9/008*   (2006.01)
(52) U.S. Cl.
    CPC .............. *A61F 2/148* (2013.01); *A61B 18/08* (2013.01); *A61F 2/142* (2013.01); *A61F 9/0081* (2013.01);

(Continued)

(58) Field of Classification Search
    CPC ....... A61B 18/08; A61B 18/082; A61B 18/10; A61F 2/142; A61F 2/148; A61F 9/0081; A61F 9/00831; A61F 2009/00872
(Continued)

(56) References Cited

U.S. PATENT DOCUMENTS 8,470,029 B2     6/2013   Walter et al.
2007/0208422 A1  9/2007   Walter et al.
(Continued)

FOREIGN PATENT DOCUMENTS

CN    101495063    7/2009
EP    1981437      10/2008
(Continued)

OTHER PUBLICATIONS

William J. Reinhart et al., Deep Anterior Lamellar Keratoplasty as an Alternative to Penetrating Keratoplasty. Ophthalmology vol. 118, No. 1, pp. 209-218, Jan. 2011, doi:10.1016/j.ophtha.2010.11.002.

(Continued)

*Primary Examiner* — Michael Peffley
*Assistant Examiner* — Khadijeh Vahdat
(74) *Attorney, Agent, or Firm* — Robert G. Lev

(57) ABSTRACT

A tool for endothelial implantation comprising a base frame on a stem and a covering frame such that the base frame is insertable between a stroma and a Descemet's membrane and the covering frame is positionable over the base frame to lockingly engage the base frame trapping a section of Descemet's membrane between the base frame and the cover frame for surgical separation of the section by cutting therearound.

5 Claims, 11 Drawing Sheets

(52) U.S. Cl.
 CPC  *A61F 9/00831* (2013.01); *A61F 2009/00872* (2013.01)

(58) Field of Classification Search
 USPC .................................. 606/33–50, 107, 166
 See application file for complete search history.

(56) References Cited

U.S. PATENT DOCUMENTS

| | | |
|---|---|---|
| 2007/0282313 A1 | 12/2007 | Huang et al. |
| 2008/0281341 A1 | 11/2008 | Miller et al. |
| 2010/0211051 A1 | 8/2010 | Weston et al. |
| 2012/0059488 A1 | 3/2012 | Shimmura |
| 2012/0245592 A1* | 9/2012 | Berner .................. A61F 2/0095 606/107 |
| 2013/0085567 A1 | 4/2013 | Tan et al. |
| 2013/0253529 A1 | 9/2013 | Walter et al. |

FOREIGN PATENT DOCUMENTS

| | | |
|---|---|---|
| JP | 2009524486 | 7/2009 |
| JP | 5312951 | 10/2013 |
| WO | WO2007089508 | 8/2007 |
| WO | WO 2007132332 | 11/2007 |
| WO | WO2007143111 | 12/2007 |
| WO | WO 2014049591 | 4/2014 |

OTHER PUBLICATIONS

John Thomas, Corneal Endothlial Transplant (DSAEK, DMEK & DLEK), Section 4 Surgical Instruments, pp. 108-119, table 11-1. Jaypee Brothers Medical Publishers Ltd, 2010 . . . .

\* cited by examiner

Cornea side

METHOD AND APPARATUS FOR ENDOTHELIAL KERATOPLASTY

PRIORITY INFORMATION

The subject National Stage application claims priority to PCT Application No: PCT/IL2013/050773, filed on Sep. 12, 2013, and Israeli Patent Application No: 222183, filed Sep. 27, 2012.

BACKGROUND

Corneal transplant surgery is required for treating for the surgical treatment of endothelial diseases of the cornea including glaucoma, edema and Fuchs endothelial dystrophy.

The cornea is the transparent front part of the eye that covers the iris, pupil, and anterior chamber. The cornea, with the anterior chamber and lens, refracts light, with the cornea accounting for approximately two-thirds of the eye's total optical power.

In humans, the refractive power of the cornea is approximately 43 dioptres. While the cornea contributes most of the eye's focusing power, its focus is fixed. The curvature of the lens, on the other hand, can be adjusted to "tune" the focus depending upon the object's distance.

Because transparency is of prime importance the cornea does not have blood vessels; it receives nutrients via diffusion from the tear fluid through the outside surface and the aqueous humour through the inside surface, and also from neurotrophins supplied by nerve fibres that innervate it. In humans, the cornea has a diameter of about 11.5 mm and a thickness of 0.5-0.6 mm in the center and 0.6-0.8 mm at the periphery. The cornea has no blood supply; it gets oxygen directly through the air. Oxygen first dissolves in the tears and then diffuses throughout the cornea to keep it healthy.

In humans (and other higher vertebrates) the cornea is fused with the skin to form a single structure composed of multiple layers.

The human cornea, like those of other primates, has five layers. From the anterior to posterior the five layers of the human cornea are:

(i) Corneal epithelium—this is an exceedingly thin multicellular epithelial tissue layer (non-keratinized stratified squamous epithelium) of fast-growing and easily regenerated cells that is kept moist with tears. Irregularity or edema of the corneal epithelium disrupts the smoothness of the air-tear film interface which is the most significant component of the total refractive power of the eye, thereby reducing visual acuity. The Corneal epithelium is continuous with the conjunctival epithelium, and is composed of about 6 layers of cells which are shed constantly on the exposed layer and are regenerated by multiplication in the basal layer.

(ii) Bowman's layer (also erroneously known as the anterior limiting membrane) is a tough layer that protects the corneal stroma, that consists of a similar irregularly arranged collagen fibers that are mainly type I collagen fibrils. These fibrils interact with and attach on to each other. The bowman's layer is eight to 14 micrometers thick.

(iii) Corneal stroma (also substantia propria). This is a thick, transparent middle layer, consisting of regularly arranged collagen fibers along with sparsely distributed interconnected keratocytes, which are the cells for general repair and maintenance. —The keratocytes are parallel and are superimposed like book pages The corneal stroma consists of approximately 200 layers of mainly type I collagen fibrils. Each layer is 1.5-2.5 µm. Up to 90% of the corneal thickness is composed of stroma.

(iv) Descemet's membrane (also known as the posterior limiting membrane) is a thin acellular layer that serves as the modified basement membrane of the corneal endothelium, from which the cells are derived. This layer is composed mainly of collagen type IV fibrils, less rigid than collagen type I fibrils, and is around 5-20 µm thick, depending on the subject's age.

(v) Corneal endothelium: a simple squamous or low cuboidal monolayer, approx 5 µm thick, of mitochondria-rich cells. These cells are responsible for regulating fluid and solute transport between the aqueous and corneal stromal compartments. The corneal endothelium is bathed by aqueous humor. Unlike the corneal epithelium the cells of the endothelium do not regenerate. Instead, they stretch to compensate for dead cells which reduce the overall cell density of the endothelium and have an impact on fluid regulation. If the endothelium can no longer maintain a proper fluid balance, stromal swelling due to excess fluids and subsequent loss of transparency will occur and this may cause corneal edema and interference with the transparency of the cornea and thus impairing the image formed.

The cornea is a protective domed layer of clear tissue covering the front of the eye. The endothelial cells are non-replicating. In normal healthy membranes there is a cell density of between about 1500 and 2500 cells per mm.

Once the population of endothelial cells decreased below a critical number that is about 600 per mm, the cornea becomes edematous while losing its optical quality. This condition is known as corneal edema.

In corneal edema, the cornea becomes overly hydrated by accumulated fluid. Corneal edema may result in deteriorated vision. If corneal edema becomes severe, blisters on the cornea can appear. In rare cases, surgery may be needed to treat corneal edema. In one technique, the cornea is replaced with a transplanted cornea.

From the functioning of the tissues in the description above it will be appreciated that corneal edema is a result of a lack of viable cells in the corneal endothelium and the purpose of a surgical transplant is to replace a section of the corneal endothelium lacking in healthy cells, with a section of donor endothelium with healthy cells.

Complete replacement of the damaged cornea has been the treatment for many years. Some disadvantages to this approach include a high degree of post-operative astigmatism, lack of predictable refractive outcome, and disturbance to the ocular surface.

Recently, the surgical trend has shifted towards removal of only a thin layer of tissue from a diseased eye and replacing it with corresponding donor tissue from a fresh human cadaver eye. The implanted tissue consists of the posterior corneal stroma, a thin layer of connective tissue known as Descemet's membrane that carries on its surface a monolayer of the endothelial cells. These cells actively "pump" the fluids from the cornea and maintain its clarity.

One such surgical technique is known as DSEK, an acronym for Descemet Stripping Endothelial Keratoplasty. DSEK is performed through a relatively small corneal incision as compared with standard perforating keratoplasty, avoiding Open sky' surgery with its risk of hemorrhage or expulsion, decreasing the incidence of postoperative wound dehiscence, and reducing unpredictable refractive outcomes. DSEK has dramatically changed treatment of corneal endothelial disease.

It is believed that DSEK and similar techniques also decrease the rate of transplant rejection. However, it will be appreciated that where the implanted tissue consists of a descemet membrane with the endothelial cells on one side and a thin layer of stroma on the other side, the implanted tissue is very fragile. When the cornea is processed pre-operatively and later during surgical implantation in the recipient eye, endothelial cell damage may be massive, and it has been estimated that on average some 30%-40% of the cells die in the first year. This is the main cause of DSEK transplant failure. Handling Descemet's membrane is required on two occasions. Firstly when the tissue is obtained from the donor cornea and secondly when the donor tissue is manipulated into the required position on the recipient's cornea. During both removal from the cadaver and positioning in the patient's eye, Descemet's membrane requires manipulation and positioning, typically with surgical blades, hooks and the like. These manipulations may cause damage to some or all of the endothelial cells themselves, resulting in immediate post-operative reduction in cell number with an accumulating cell number decrease over the first year due to death of the partially damaged cells. This diminishes the likelihood of a long term successful surgical outcome.

Eye banks have been providing full thickness corneas for surgical transplantation for many years. With the trend towards replacement of a thin membrane only, by Descemet's stripping automated endothelial keratoplasty, (DSAEK) and to minimize the damage thereto, the donor membrane has been removed from the donor eye in theatre and immediately inserted into the patient's eye behind the cornea.

Since about 2006, eye banks have developed methodologies for precutting the center of the donor corneal tissue at the eye bank for subsequent use in surgery. For most corneal surgeons, the availability of such precut corneal tissue saves time and money, and reduces the stress of performing the donor corneal dissection in the operating room.

In surgery, a circumferential incision is made in the side of the cornea. A tool is used to cut through Descemet's membrane and to detach it by upwards scraping a section, marked by ink on the corneal outside surface. The detached section is then removed through the incision. The replacement membrane from the donor is trephined out of the precut area of the donor cornea and the round thin graft is inserted through the incision, manipulated into position and then floated up into the scraped area by releasing an air bubble under the replacement membrane. This bubble is later absorbed into the eye fluid and disappears.

Successful endothelial implantation procedures provide excellent visual outcomes due to the minimal change in corneal surface topography or refraction. They can successfully treat corneal dysfunction associated with Fuchs' endothelial dystrophy, bullous keratopathy, iridocorneal endothelial syndrome or a failed penetrating graft.

To minimize the damage to the corneal optical quality, the corneal incision is preferably as short as possible and the diseased descemet's membrane must be folded to remove it through the short incision. The replacement Descemet's membrane must also be folded to introduce it through the incision. It will be appreciated that the manipulation of the donor Descemet's membrane into the patient's eye via a short incision, that is typically about 6 mm on average, with minimal damage to the endothelial cells, is a highly skilled task and requires highly skilled eye surgeons, making the surgery difficult and expensive.

SUMMARY

A first aspect of an embodiment is directed to providing a tool for endothelial implantation comprising a base frame on a stem and a covering frame such that said base frame is insertable between a stroma and a Descemet's membrane and said covering frame is positionable over said base frame to lockingly engage said base frame trapping a section of Descemet's membrane between the base frame and the cover frame for surgical separation of said section by cutting therearound.

Typically, said base frame and said cover frame are circular.

In some embodiments, one of said frames is provided with male coupling elements and the other of said frames is provided with corresponding female coupling elements.

Optionally, said male elements are pegs and said female elements are socket holes.

Optionally, the pegs are split pins.

In some embodiments, a piece of Descemet's membrane from a donor is trappable between said base frame and cover frame, and may be separated from surrounding tissue by cutting around the frame.

In some embodiments, the frame is coupled by the stem to a lid and the lid is sealingly attachable to a container of solution such that a specimen of Descemet's membrane is sealingly preservable in said solution for a time period.

Some embodiments further comprise a heating element in one of said frames, and connecting wires couple said heating element to a power supply via a switch such that activation of the switch burns perimeter of membrane and releases the Descemet's membrane from the frame.

In some embodiments the stem provides fluid communication between at least one outlet in said frame and a reservoir of fluid within an injector and injection of said fluid from said injector releases said fluid below said membrane specimen.

In some embodiments the fluid is a gas and said gas forms at least one bubble that causes said detached membrane to be floated into position.

Some embodiments further comprise a pair of wires coupling said frame to said injector via said stem such that a force on said wires causes said stem to curl up.

A second aspect of is directed to a method of surgically replacing a section of Descemet's membrane comprising the steps of:

Obtaining a section of Descemet's membrane using the tool of the invention by separating the donor membrane from the stroma, inserting the base ring under the donor membrane, lowering the upper ring over the lower ring and engaging them together; storing the donor membrane if necessary.

Making incision and removing a damaged Descemet's membrane from a patient via the incision;

Curving the pair of rings and bending the donor membrane;

Inserting the rings and donor membrane through incision into the eye;

Releasing curving pressure to straighten the rings;

Applying current to detach donor membrane from rings;

Bubbling air under donor membrane to float up into position;

Curving the rings and extracting through the incision, and

Suturing the incision.

BRIEF DESCRIPTION OF FIGURES

For a better understanding of the invention and to show how it may be carried into effect, reference will now be made, purely by way of example, to the accompanying Figures, wherewith it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

DESCRIPTION OF PREFERRED EMBODIMENT

Figure 1:
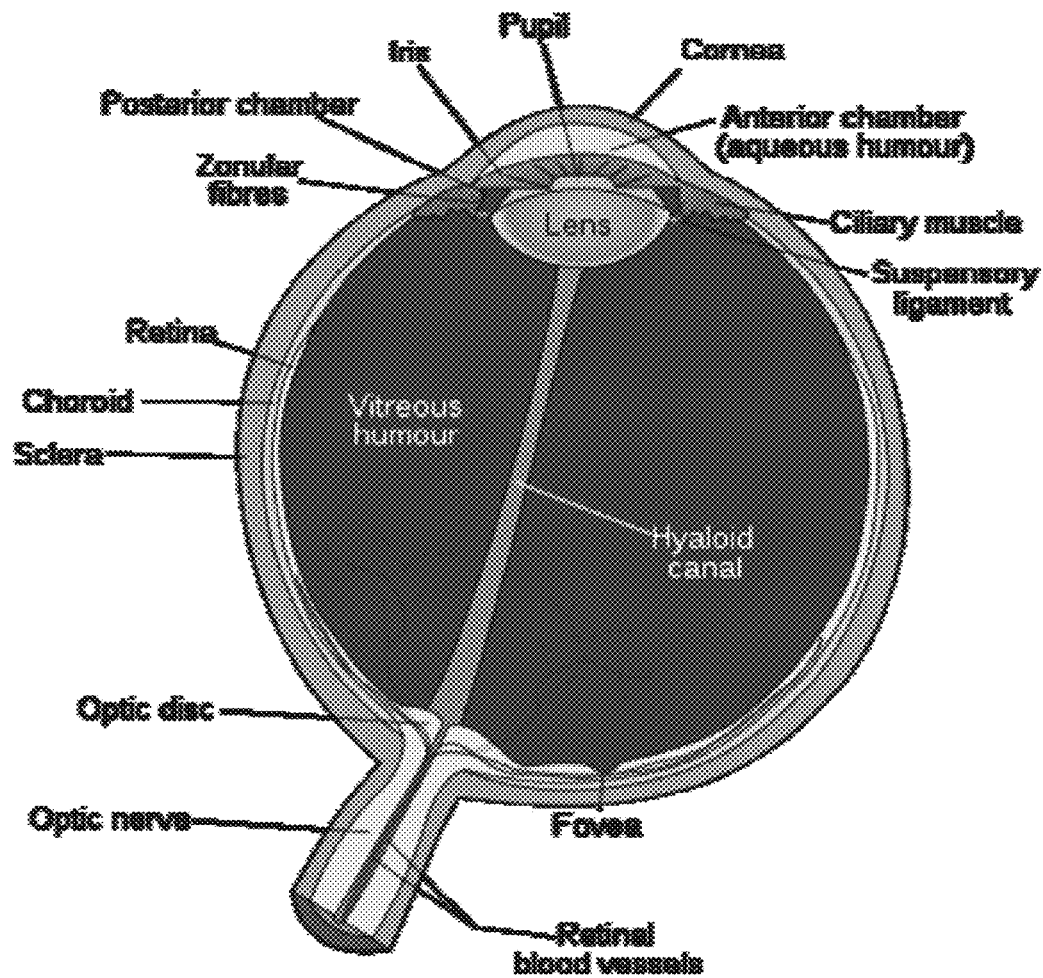
FIG. 1 is a schematic cross-sectional view of a human eye with the cornea facing upwards, in the position during surgery (prior art)

FIG. 1 is a schematic illustration of an eyeball.

Figure 2:
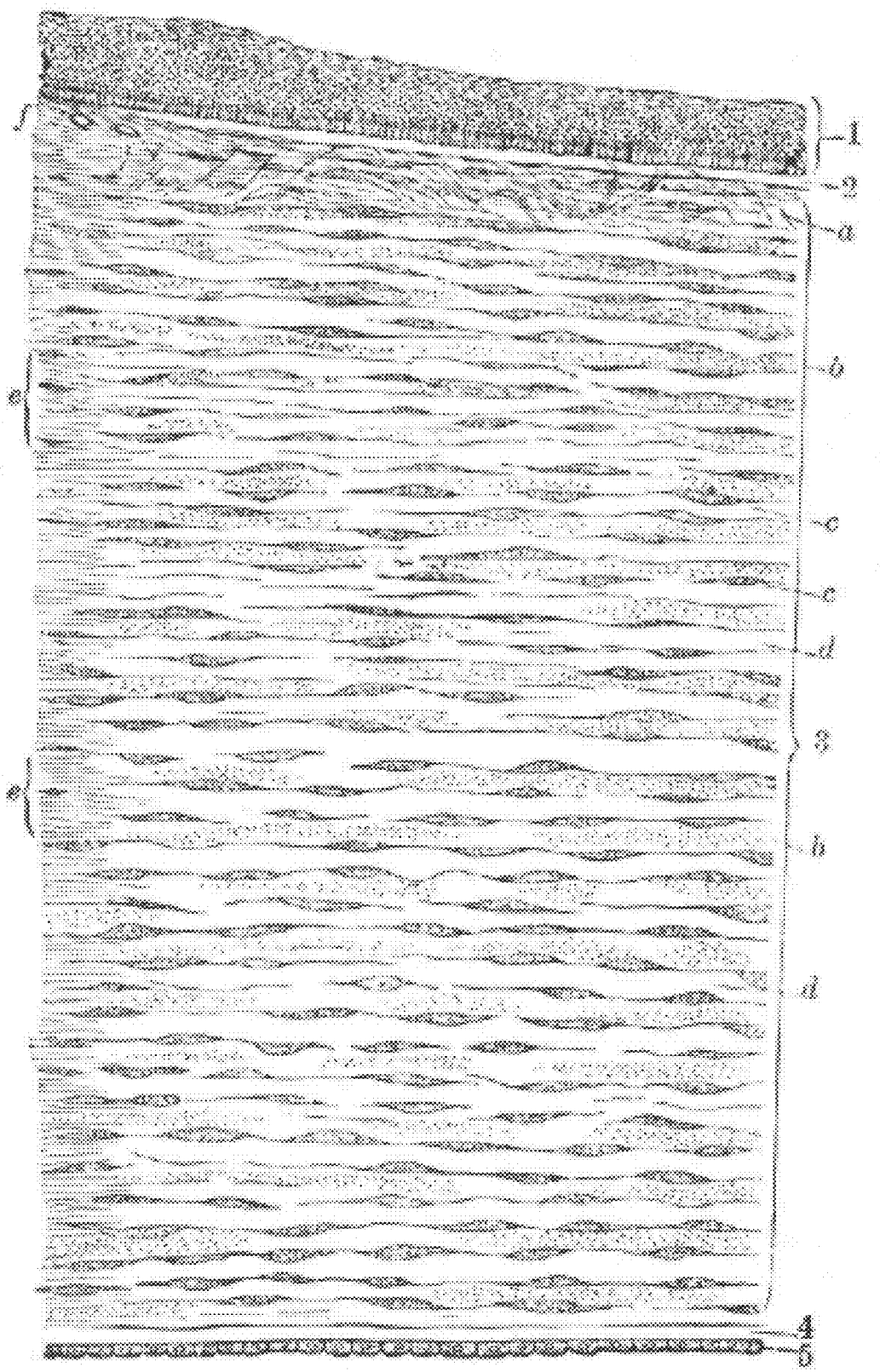
FIG. 2 is a vertical section of human cornea (taken from Gray's Anatomy) from near the margin (magnified), and showing the various layers of the cornea.

FIG. 2 is a vertical section of human cornea from near the margin (magnified) and showing the 1. Epithelium, 2. Anterior elastic lamina, 3. substantia propria, 4. Posterior elastic lamina (Descemet's membrane), 5. Endothelium of the anterior chamber, a. Oblique fibers in the anterior layer of the substantia propria, b. Lamellae the fibers of which are cut across, producing a dotted appearance, c. Corneal corpuscles appearing fusiform in section, d. Lamellae the fibers of which are cut longitudinally, e. Transition to the sclera, with more distinct fibrillation, and surmounted by a thicker epithelium, and f. Small blood vessels cut across near the margin of the cornea.

Embodiments, of the present invention are directed to improved tools and techniques for endothelial implantation, by techniques such as DSAEK—Descemet's Stripping Automated Endothelial Keratoplasty, DESK and DEMK, for example.

The tools and techniques of the present invention are directed to removing the Descemet's membrane from the donor eye, storing it until required, and inserting it and positioning it in a patient's eye, whilst minimize damage to the membrane.

Tools of the invention minimize the handling of the donor Descemet's membrane to maintain a high number of viable endothelial cells during preparation and storage, keeping the tissue stored in a ready for implantation state, eliminating the need for direct contact with the implanted tissue during the surgical implantation phase.

In contradistinction to prior art techniques, the removal of the donor Descemet's membrane from the donor cadaver eye may be performed in advance, and does not need to be performed in surgery. With reference to FIGS. 3a-g, a first technique for removing a Descemet's membrane from a donor eye is shown. The first technique uses direct mechanical separation of Descemet's membrane from the corneal stroma by pressurizing a fluid which may be air, liquid such as water, a viscoelastic fluid or a combination of these elements via a fine cannula with a blunt tip, to avoid puncturing Descemet's membrane during its positioning. The pressurized fluid cleaves between the stroma and Descemet's membrane.

Figure 3A:
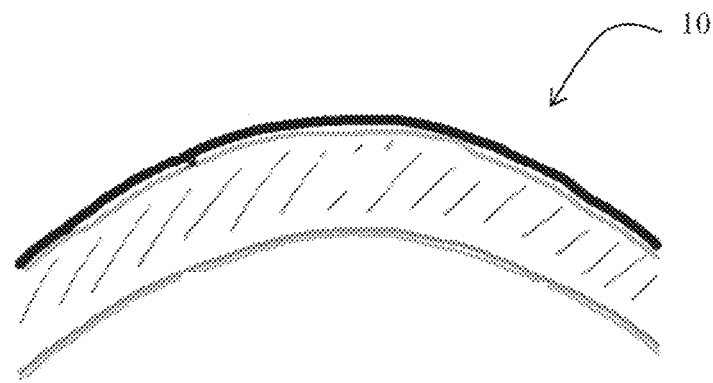
FIG. 3a is a simplified schematic view of a section of the cornea, eye facing upwards, as in a cadaver lying on back.
Figure 3B:
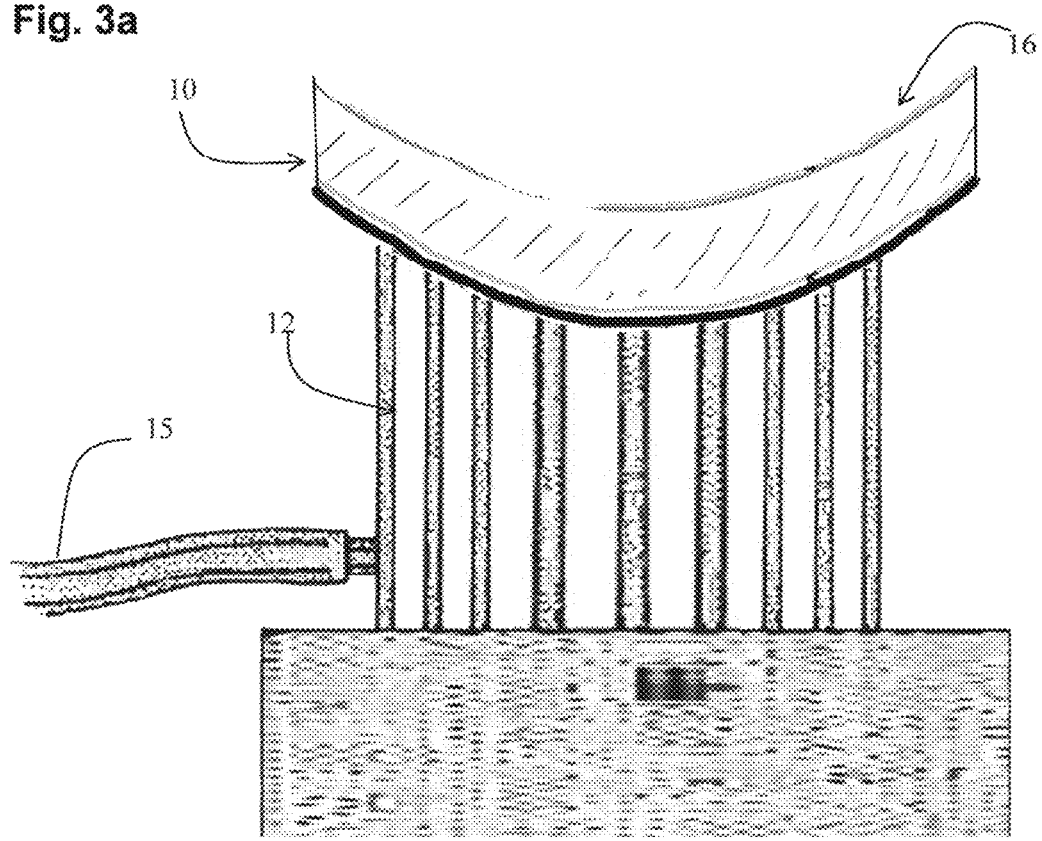
FIG. 3b is a schematic cross section showing the section of the cornea inverted and placed on a vacuum holder.

With reference to FIG. 3b, a section of a donor cornea 10 inverted on a stand 12 is shown. The cornea 10 is positioned with Descemet's membrane 16 facing upwards. A pipe 15 connected to a vacuum pump may be used to provide vacuum suction to hold the donor cornea 10 to the stand 12.

Figure 3C:
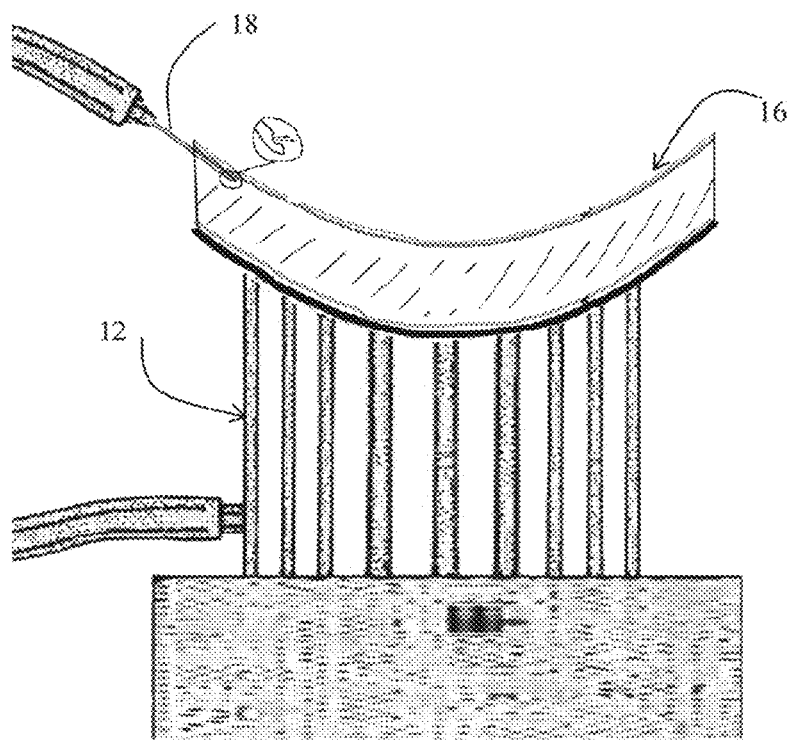
FIG. 3c is a schematic cross section showing how a blunt needle probe may be inserted into the section of the cornea under the Descemet's membrane.
Figure 3D:
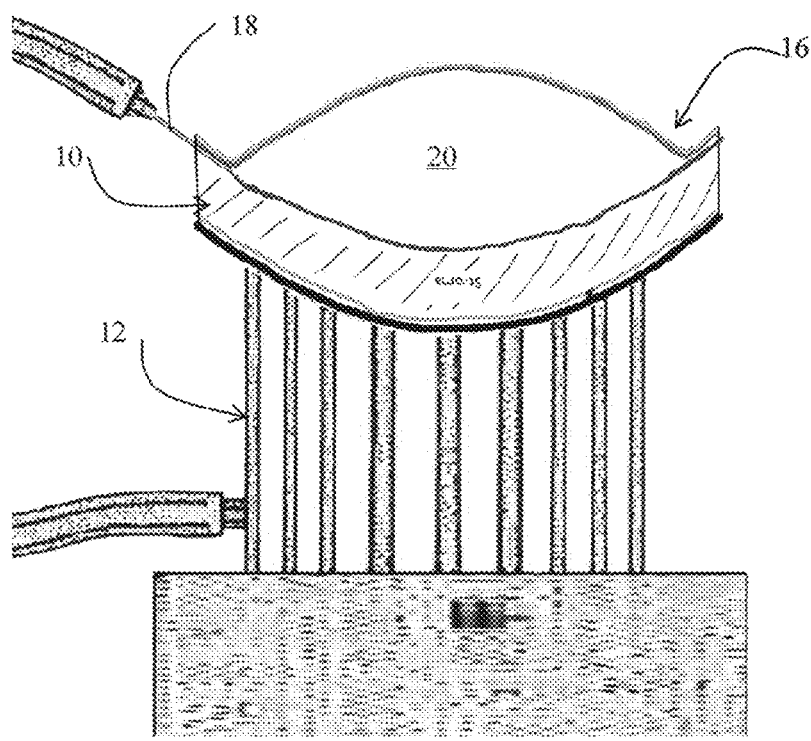
FIG. 3d is a schematic cross section showing how a cavity may be formed under the Descemet's membrane by pumping fluid from blunt probe under the Descemet's membrane, detaching it from the stroma.

In FIG. 3c a cannula 18 with a blunt tip is shown, positioned so that the blunt tip and outlet of the cannula 18 is within the cornea, under the Descemet's membrane 16. As shown in FIG. 3d, air or liquid, such as water or an opthalmic solution is injected through the cannula 18, producing a cavity 20 at the end of the cannula 18 that literally tears the Descemet's membrane 16 away from the stroma of the cornea 10.

Figure 3E:
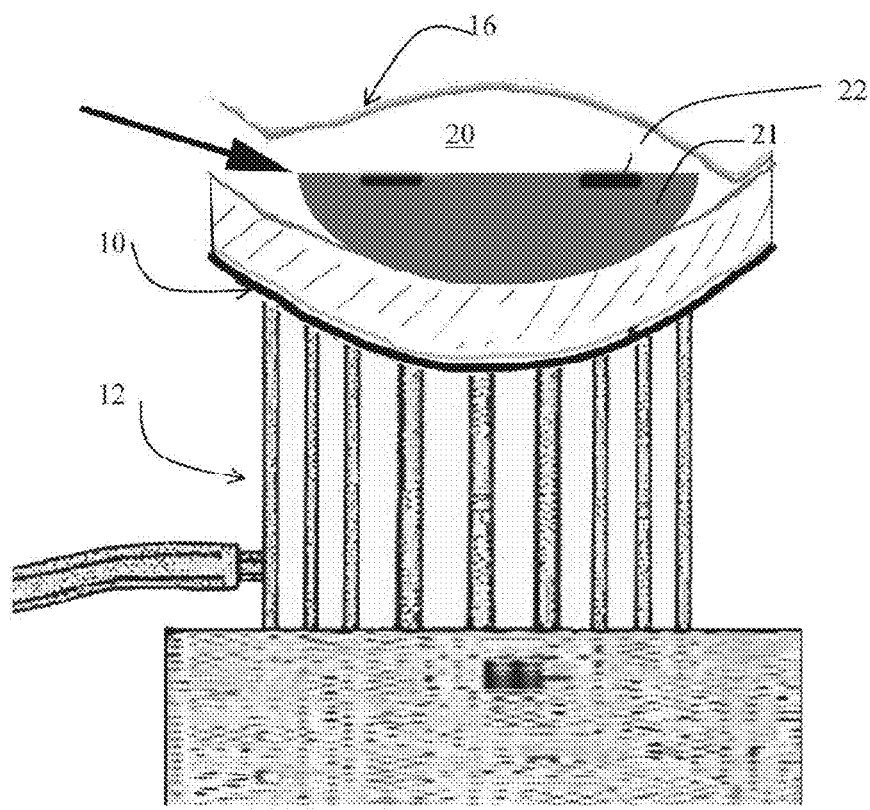
FIG. 3e is a schematic cross section showing how a base and ring may be inserted into the cavity.

FIG. 3e discloses a framework for handling Descemet's membrane. In one embodiment, the framework includes a ring 22 on a base 21, which may be inserted in the cavity 20 between the Descemet's membrane 16, and the rest of the cornea 10 created by the injected fluid. The base 21 is typically a section of a sphere having appropriate curvature to the stroma and a flat upper surface with a socket for the ring 22.

Figure 3F:
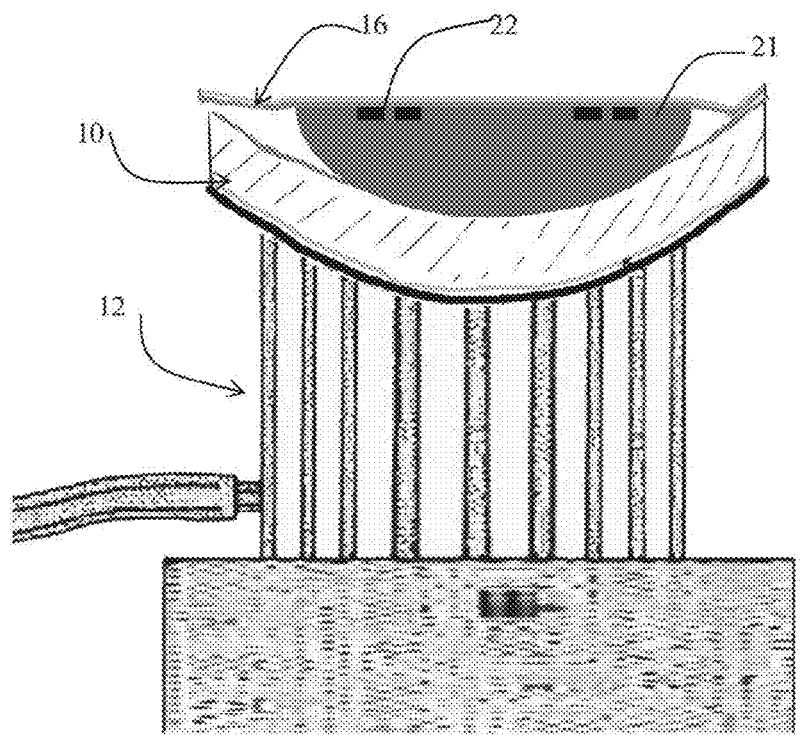
FIG. 3f is a schematic cross section showing how Descemet's membrane may be stretched over the base and ring.

As shown in FIG. 3f, by removing the fluid from the cavity 20, the Descemet's membrane 16 may be stretched taut over the ring 22 on the base 21.

Figure 3G:
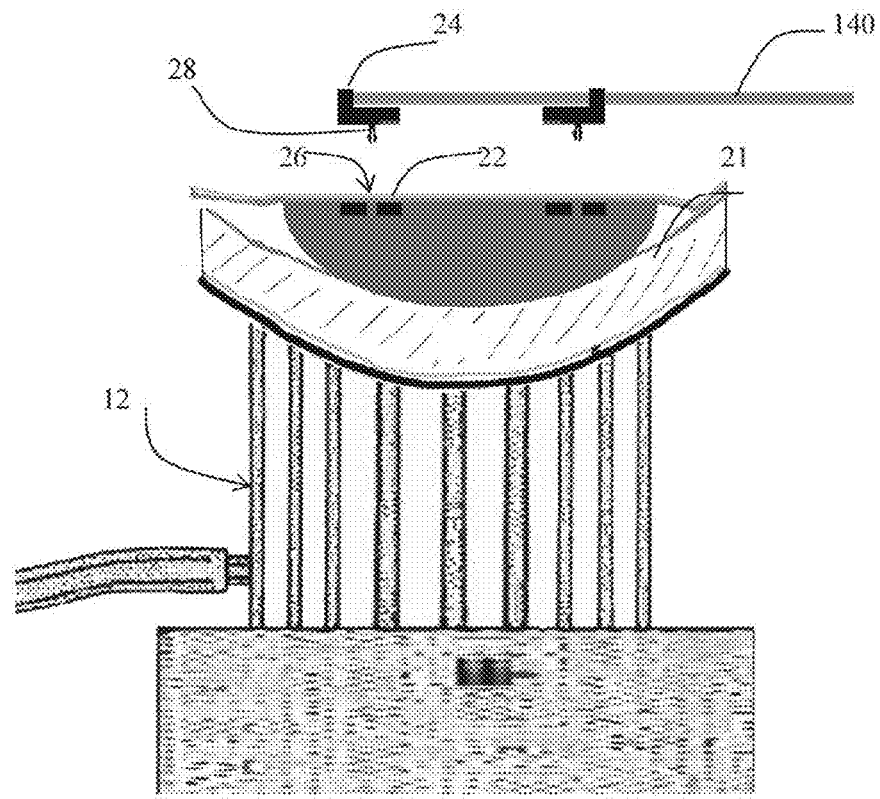
FIG. 3g shows how a cover ring with protruding pegs may be lowered onto the base and ring, such that the pegs may engage socket holes in the ring.

FIG. 3g is a schematic view showing how a second ring 24 may be lowered over the first ring 22 to engage the first ring 22, trapping a circular disk of Descemet's membrane 16 between the two rings.

Preferably the two rings 22, 24 are configured to lockingly engage each other. In one embodiment, the first ring 22 is provided with a series of holes 26 and the second ring 24 is provided with a series of posts 28, which may be aligned with the holes 26 and lowered to engage the holes 26, locking the first 22 and second 24 rings together, trapping a disk of Descemet's membrane 16 therebetween.

As shown in FIG. 3g in some embodiments, post 28 may be a pair of split pins to lockingly engage the hole 26. In some embodiments, posts may be provided on the first ring 22 and holes 26 may be provided on the second ring 24.

Pin and hole connectors are just one option for coupling the two rings together about a piece of Decimet's membrane 16. For example, in an alternative (not shown), a tongue may be provided on the facing surface of one of the rings and a groove provided on the corresponding face of the other ring.

Figure 4:
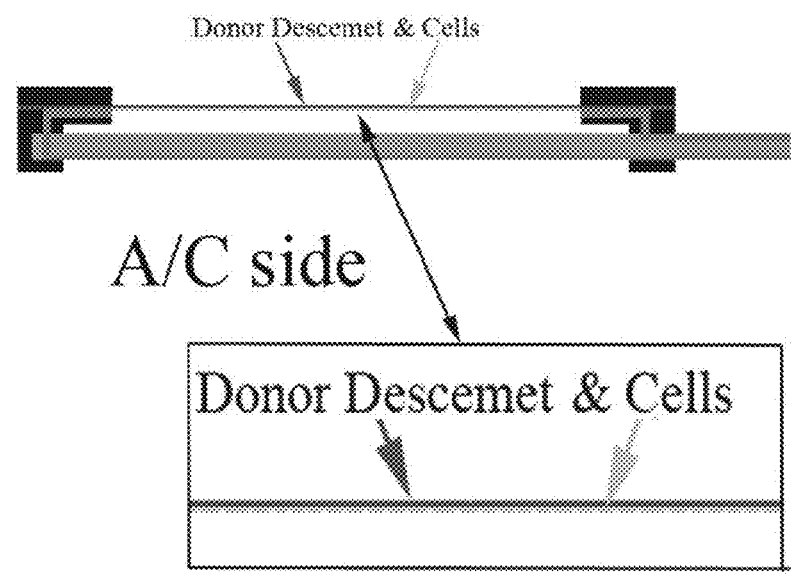
FIG. 4 shows the base and cover ring in more detail from various angles.

With reference to FIG. 4, once a disk of Descemet's membrane 16 is clamped between the two rings 22, 24, it may be detached from the surrounding tissue of the cornea 14 with a scalpel or with a circular cutter, for example. In this manner, a disk shaped piece of Descemet's membrane 16 may be removed from a donor eye 10 by contacting the perimeter only without touching either surfaces of the membrane 16, thereby minimizing damages to the epithelial layer.

Figure 3H:
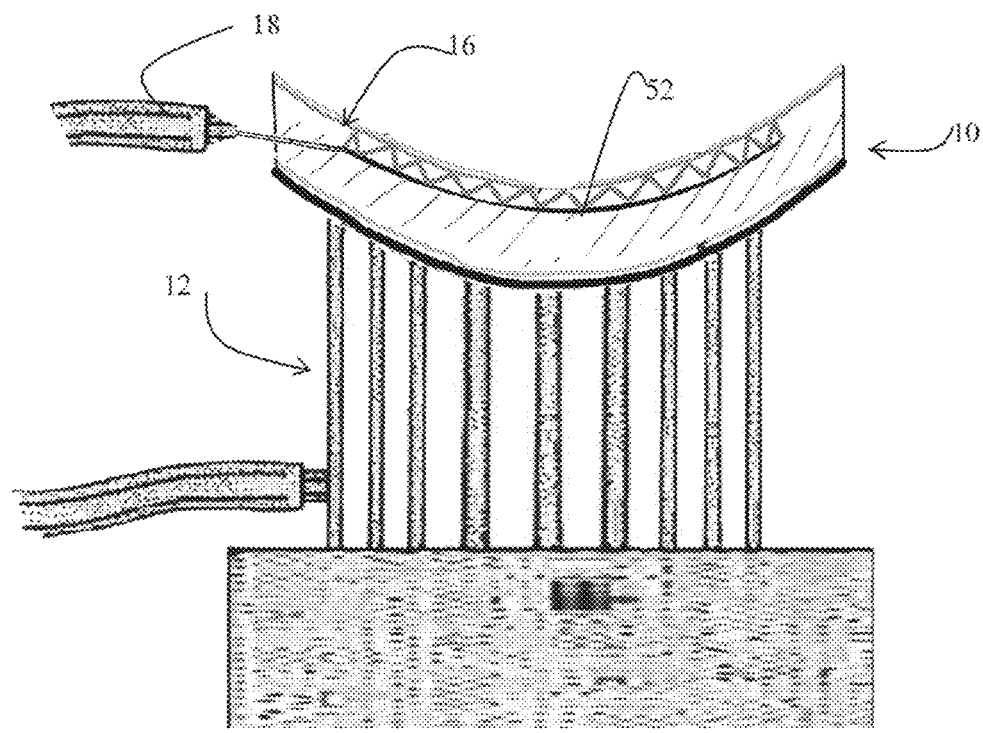
FIG. 3h shows an alternative technique for preparing a donor cornea, that uses an advanced high frequency laser to cut an accurate cleavage in the donor's cornea before removal of the cornea from the eyeball.

A second technique uses an advanced high frequency laser to cut an accurate cleavage 52 in the donor's cornea 10 while the whole eyeball is fixated in a holder, before removal of the cornea from the eyeball. This type of procedure is currently being used to prepare the flap cleavage during refractive surgery, for example. With reference to FIG. 3h, once the cleavage 52 is cut by the laser at a precise distance from the Descemet membrane 16 and into the stroma, the cornea 10 including the typical scleral ring is removed from the donor eye and positioned on a vacuum stand with the endothelial cells upwards. The laser induced cleavage is then filled with air or fluid or viscoelastic using the blunt tip cannula 18 and the entry site is widened to enable the insertion of the ring holder into the cleavage 52 and the process continues as described for the first separation method.

The second method as illustrated in FIG. 3h is important as it enables implants with designed thickness to be prepared. This is useful since some corneal pathology extends to the deeper stroma and replacement of the endothelial cells only is insufficient to provide the needed optical clarity. Measuring the location of such lesions in the deep sclera enables the graft thickness to be accurately prepared by these lasers and the implanted tissue will thus exactly match the diameter and thickness of the cleavage in the recipient eye which may also be prepared using the same laser technology.

Figure 5:
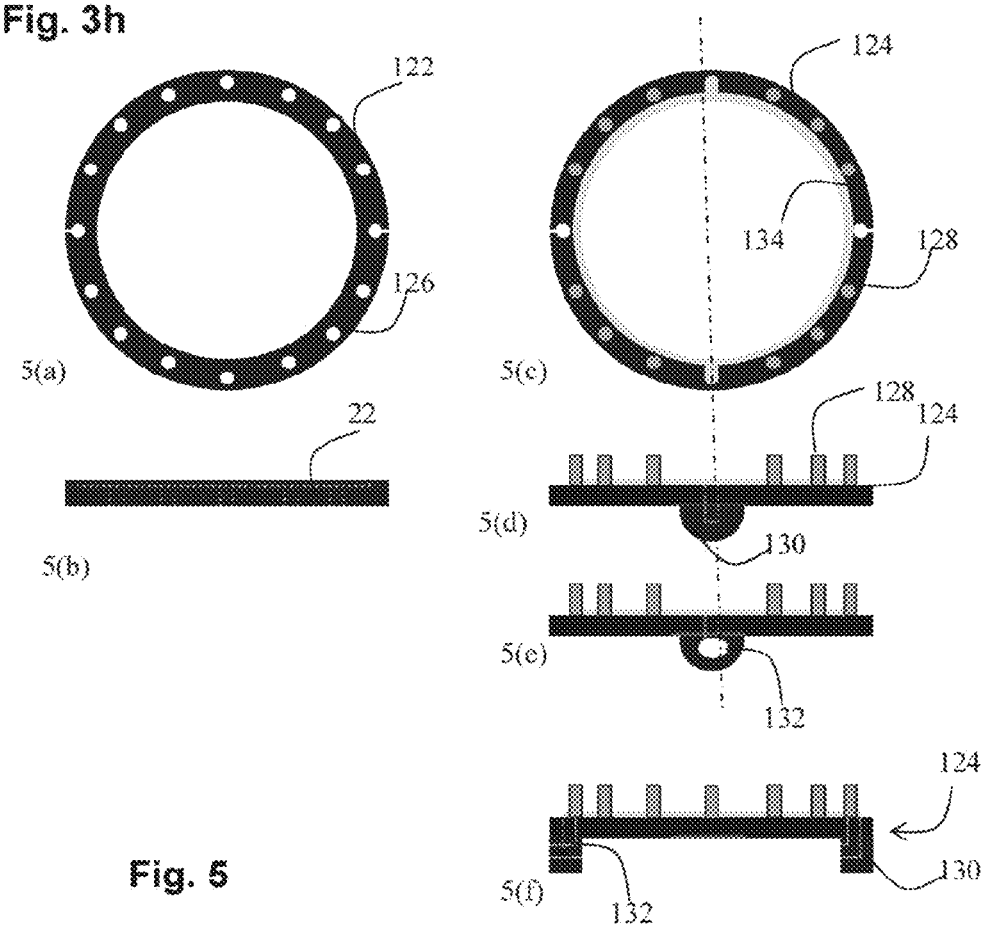
FIG. 5 shows how the donor Descemet's membrane may be trapped between the base and cover ring.

With reference to FIG. 5, the base ring 122 and cover ring 124 of one embodiment are shown in more detail. FIG. 5(a) shows the base ring 122 from the top and FIG. 5(b) shows the base ring from the side. Base ring 122 is provided with a number of holes that serve as sockets for engaging corresponding pegs 128 that are provided on a corresponding cover ring 124 shown in FIG. 5(c) from above and in FIGS. 5(d)-(f) from the side.

In FIG. 5(d), one end of the cover ring 128 is weakened in the middle and is provided with a hinge 130 enabling it to fold in half along ifs diameter.

As shown in FIG. 5(e), at the opposite end of the diameter there is a corresponding hinge that includes a conduit 132. FIG. 5(f) shows cover ring 128 from the side.

Referring back to FIG. 5(c), the cover ring 124 is further provided with an electrically connecting, high resistance inner ring 134.

It will be appreciated that in alternative embodiments, features associated with base ring 122 (such as socket holes 126) may be provided in a cover ring, and features associated with cover ring 124, such as electrically connecting, high resistance inner ring 134, may be provided with a base ring.

Figure 6:
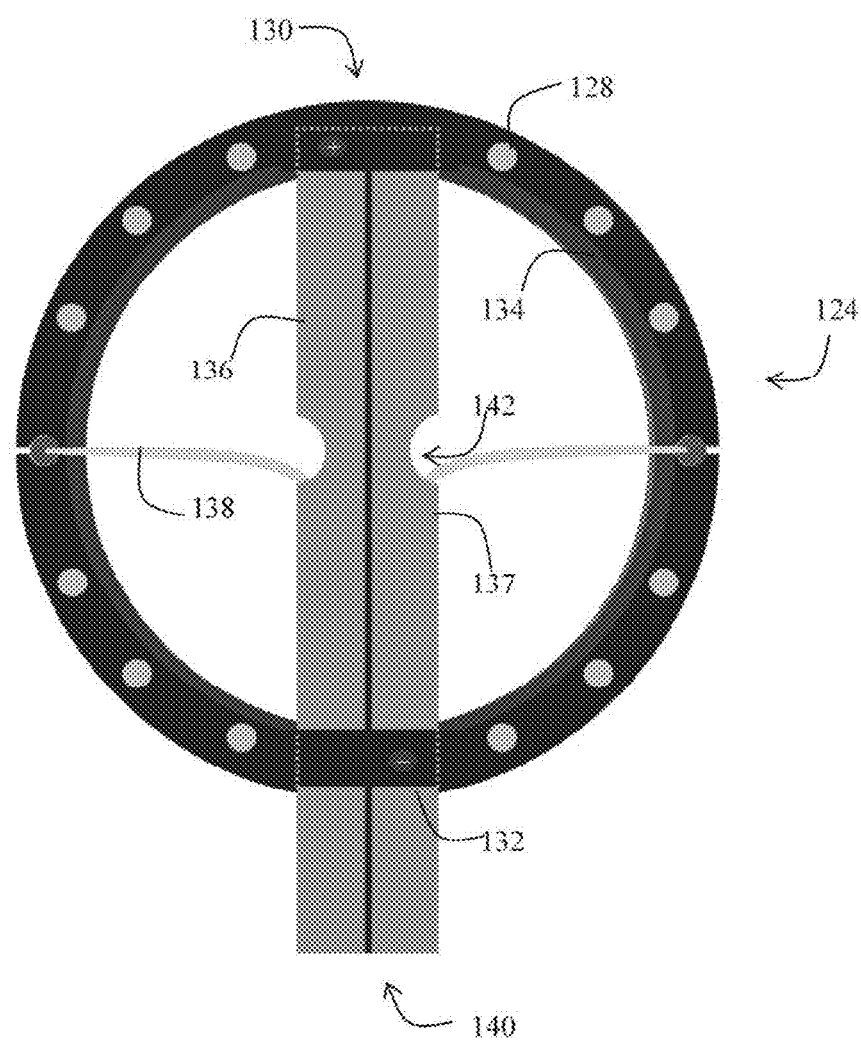
FIG. 6 is a schematic illustration of the base and cover ring as part of a positioner including: (i) a conductive inner ring and a connecting rod for selectively providing a pulse to the conductive inner ring to burn through and detach the membrane, (ii) wires for folding the rings that are manipulated via the connecting rod, and (iii) fluid conduits built into the connecting rod for releasing air bubble under the Descemets membrane for floating the membrane to its application site.

Referring now to FIG. 6, an enlarged view of the cover ring 124 is shown, on its holder 140. Holder 140 may include a pair of hollow tubes 136, 137 through which a fluid, typically a gas, may be passed. A pair of micro-cables 138 pass through hollow tubes 136, 137 and couple to the cover ring 124 at a distance from the hinges 130, 132, preferably orthogonal thereto. The hollow tubes 136 137 also serve to carry a current to the electrically connecting, high resistance inner ring 134.

If the cover ring 124 (or indeed the base ring 122) is provided on a stem 140, the assembly comprising the pair of rings 122, 124 on the stem 140 with a trapped Descemet's membrane 116, harvested from a donor eye, may be lowered into a jar filled with a standard clinically approved preserving solution that may be used for corneal preservation, and the lid closed to the jar, to seal it, protecting the tissue 116 from contamination and keeping it moist in an appropriate preservation solution.

In this manner, a specimen disk 116 of Descemet's membrane 16 may be removed from a donor eye 10 and stored until needed.

The above described assembly 140 is a convenient way of obtaining a quality section of Descemet's membrane 116.

The ring assembly otherwise known as a positioner, consists of 2 semi flexible frames 122, 124 fabricated from a biocompatible nonconductive material such as PTFE or HDPE. Each frame is preferably a few hundred microns thick, perhaps 0.5 mm thick, and defines an inner space of the clinically favored implanted tissue size, which is currently between about 7.0 mm and 8.0 mm. Typically, the frames 122, 124 are circular and the space they define is a disk shape. Other shapes, such as ellipses and oblongs, are also possible.

The outside diameter of the rings 122, 124 must be sufficient to maintain their round shape and to be semi-rigid. Preferably, the outer diameter of the rings is about 9.0 mm to 10.0 mm. Preferably the two rings 122, 124 have the same inner and outer diameters. They are provided with thinner sections or other adaptations that enable them to fold along their access. The rings 122, 124 are designed to physically engage each other when brought into contact. One preferred mode of interlocking is a pin 128 and hole 126 arrangement where one ring 124 carries short pin like structures 128 on its surface that are inserted into a matched holes 126 on the other ring 122. In one embodiment, as shown in FIG. 3(g), one ring—in this case the cover ring 24 is provided with pegs 28 that may usefully be split pins, and the other ring—in this case, the cover ring 22, is provided with corresponding sockets 26.

The pegs 28 may be inserted into the sockets 26 to attach the cover ring 24 to the base ring 22 coupling the two rings together. Other interlock mechanisms, such as tongue and slot mechanisms, may be used to enable the base and cover rings to engage each other, in a manner minimizes surface sliding between the rings when the pair of joined rings is flexed.

To ensure locking, the pegs 28 may be split pins that frictionally engage the holes or sockets 26 into which they are positioned. Alternatively one ring may be heat treated to soften the polymer such that cooling to room temperature causes it to shrink, or it may be cooled, so that warming to room temperature causes it to expand.

Preferably one or other or both rings are fabricated from a hydrogel polymer so that storage in an aqueous solution causes them to swell and to tightly interlock.

The stem 140 is a rigid structure that is typically about 30 mm to 50 mm long and 0.5 mm to 1.0 mm in outer diameter and is preferable of tubular shape with an oval cross section. The stem 140 is fixed to the surface of one of the semi-flexible rings, typically to the base ring 22.

An embodiment of the present invention is directed to providing a toolset that includes the above mentioned assembly, but is designed to implant the Descimet's membrane into a patient's eyeball with minimum handing and risk of damage to the membrane 16.

With reference to FIG. 6, in one embodiment, therefore, The stem 140 is provided with one or more outlets 142, so that fluid, whether air or liquid, supplied via the tubes 136, 137 may be bubbled out of the outlets 142 under the Descimet's membrane.

Furthermore, the base ring and cover ring 124 may be provided with hinges 130, 132 that may be simple fold lines, along the diameter where the stem 140 is affixed, such that the ring pair 122, 124 may be folded along this diameter about these hinges 130, 132.

Hinges 130, 132 may be created in a number of ways. For example, by local thinning of the material from which the base ring 122 and cover ring 124 are constructed. Additionally or alternatively, the hinges 130, 132 may be created by local softening of the material, or by fabricating the ring 122, 124 from two parts coupled with a pair of hinges or from rings with weakening fold lines.

In one embodiment, a folding mechanism may be provided. The folding mechanism may include a couple of micro-wires 138 that couple to the ring 124 at a distance from the hinges 130, 132, and preferably if the fold lines 130, 132, are considered as being at 12 and 6 O'Clock, that micro-wires 138 will connect to the ring 124 at about 3 O'Clock and 9 O'Clock. The far ends of the wires 124 may couple to a lever positioned on the stem 140, such that manipulation of the lever causes a pressure to be exerted on the micro-wires 138 to flex the rings 122, 124 and fold them slightly.

It will be appreciated that for insertion into a patient's eye, an incision is required in the cornea. By enabling the pair of rings 122, 124 to be folded, the pair of rings 122, 124 and Descimet's membrane 116 trapped therebetween may be inserted through a small incision into a patient's eye.

It will be noted that folding a detached section of a patient Descemet's membrane for removal via a circumferential incision in the cornea and insertion of a donor membrane 16, is known. However, in the prior art the membrane is folded and unfolded using hooks and blades, and a number of epithelial cells become damaged in the process.

Figure 7:
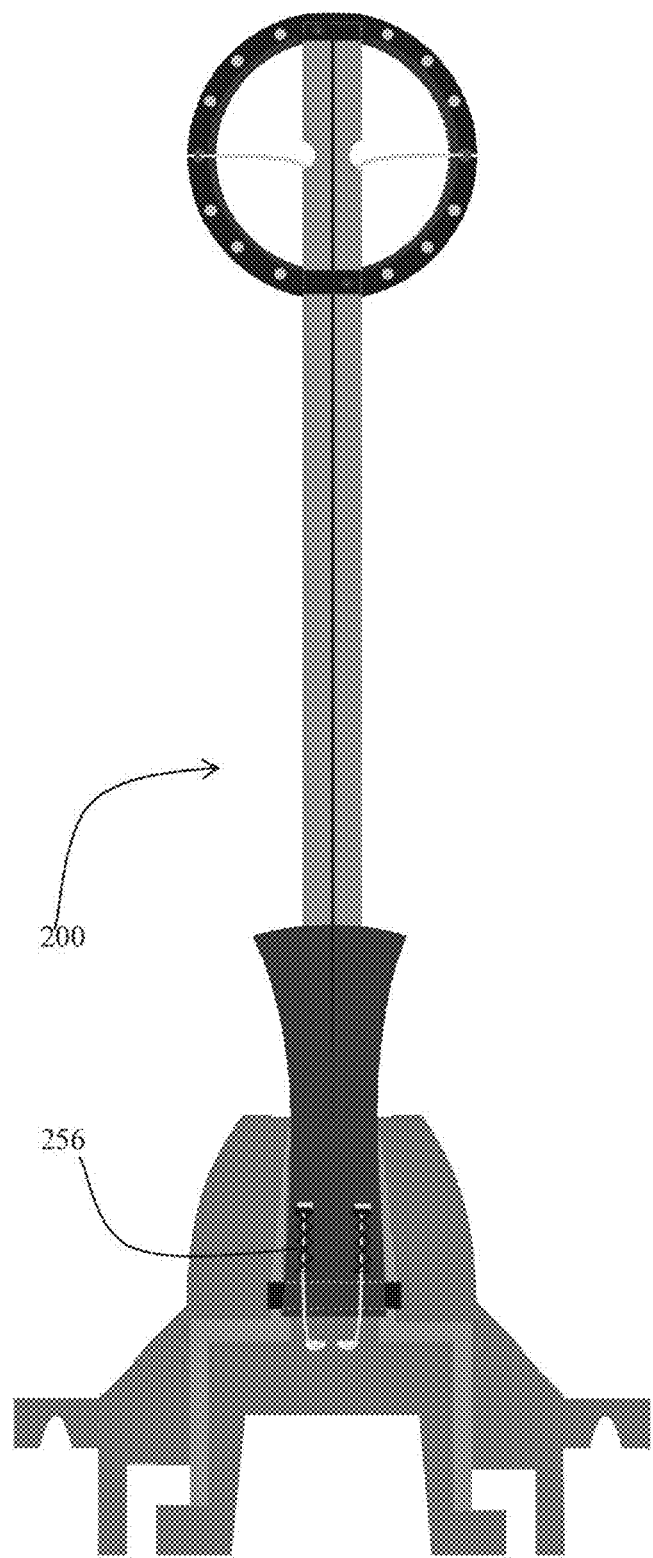
FIG. 7 is a schematic section through the positioner, which may be sealingly inserted into a jar of fluid to keep donor Descemet membrane sample clean and fresh, or coupled to an applicator for applying the donor Descemet's membrane to a patient.
Figure 9:
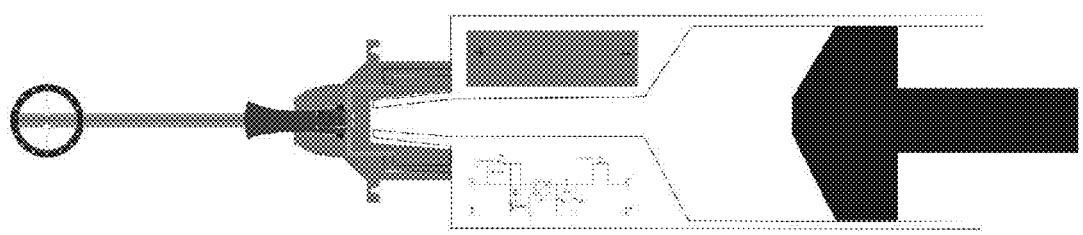
FIG. 9 is a section through the positioner of FIG. 7 connected to a handle comprising a micro-syringe for providing air bubble under the descemet's membrane, and including the electronics and power supply for applying the pulse to the conductive inner ring required to detach the membrane.

With reference to FIG. 7, the positioner 200 is designed for coupling to a fluid injector 250 shown in FIG. 9. The positioner 200 and injector 250 may be provided as a single component or as separate components, which may be easier to sterilize and more convenient. A lever 256 may be affixed to the positioner 200 and operated by the thumb or by a finger, or may be dispensed with altogether, since if the wires 138 are coupled to the base of the positioner 200, pressure on the stem 140 may be sufficient to cause the rings 122, 124 to fold.

Thus in some embodiments, a pulling mechanism consisting of fine strong wire 138 made of a synthetic polymer, metal or other biocompatible material that are anchored to the outer edges of either of the joined semi-flexible nonconducting rings 122, 124 at points distanced from the stem 140, is provided. The wires 138 pass through small holes 142 in the stem sides 136, 137 and are connected with a lever 256. Pulling the lever 256 applies a deformation force via these wires which causes the rings 122, 124 to flex and results in their folding inwards by pulling at two points opposite to each other and enables a deforming force to be applied to the edge of the ring pair, causing the ring to curl.

By curling the rings, they may be inserted through short slits in the cornea, during surgery.

For sterilization purposes it may be preferable for the ring assembly and the injector to be separate components that may be joined together, preferably by an interlock mechanism, prior to implantation. As shown in FIG. 9, the positioner 200 and the injector 250 may alternatively be provided as a single unitary tool.

Figure 8:
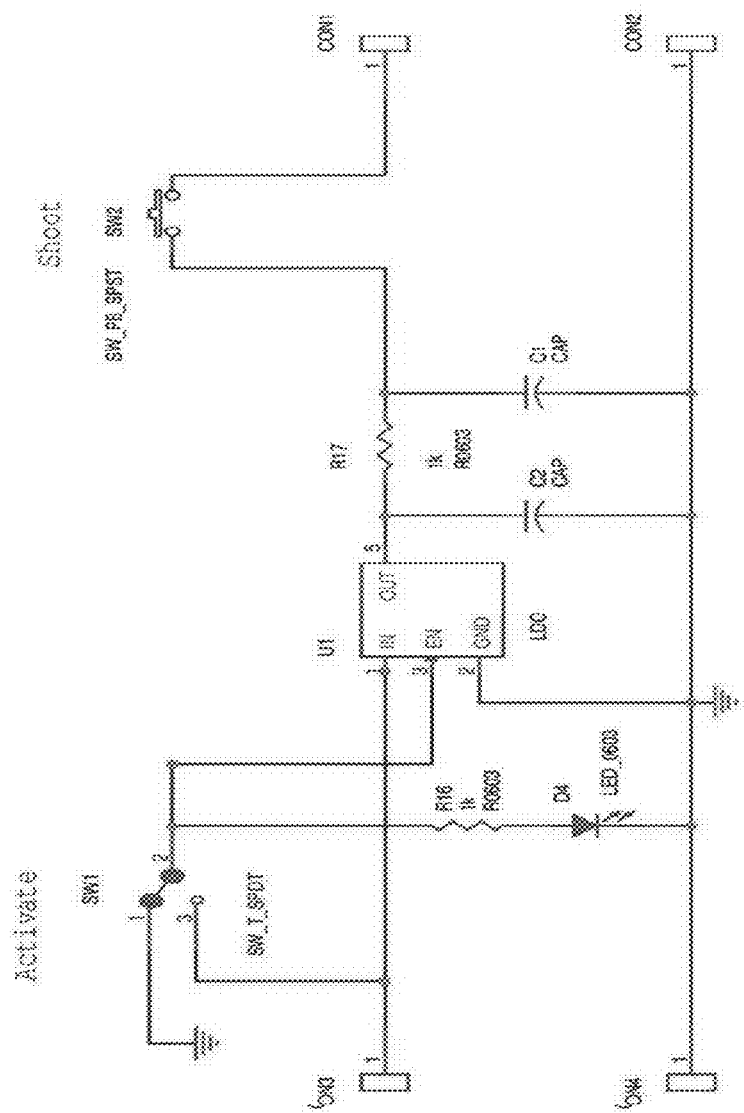
FIG. 8 is a circuit diagram of an electronic circuit for applying a pulse to the conductive inner ring to burn through and detach the membrane.

Referring to FIG. 6, one ring, typically the cover ring 124 is further provided with a torroidal element of a biocompatible, electrically conducting material with high resistance known henceforth as a heating element 134. The heating element 134 is coupled via micro-tubes 136, 137 which are current carriers, to a power supply so that current may be passed therethrough. A capacitor circuit 254, shown in FIG. 8 is provided, either in injector or separate thereto. A short high current pulse is passed through the heating element 134. This generates heat and burns through a membrane 16 clamped between the two rings 122, 124, thereby releasing a donor tissue sample 16 clamped therebetween.

Wires coupled to the element 134 may pass along the stem 136, 137 and be connected to a power source 258 within the injector 250, or to a separate power source coupled therewith.

Torroidal heating element 134 is fabricated from a high resistance biomaterial such as a Nickel Chromium alloy. Where the injector 250 is detachably coupleable to the positioner 200 assembly, contact points on each component may be aligned on assembly.

Thus the torroidal heating element 134 is electrically coupled to electrical conducting wires of lower resistance, for example copper, that extend along the stem 140. These wires may be positioned on the outside or on the inside of the stem 140 or may be incorporated in the wall structure of the stem 140. The connection between the stem 140 and the semi-flexible polymer rings 122, 124 enables the polymer rings 122, 124 to be positioned and manipulated.

Where the stem 124 itself is metal, the electrical wires are jacketed to insulate them therefrom. Where the positioner 200 and injector 250 are separate components, the wires on the stem 140 may be terminated with connectors for connectively engaging corresponding connecting elements on the injector. Thus coupling the injector to the positioner requires a mechanical coupling mechanism for attaching the injector 250 to the stem 140, and electrical contacts for providing electrical connections for allowing a current to be supplied to the heating element 134.

In a variant assembly, the connecting apparatus comprises of a two level structure. The lower level contains a holding element for the connecting element with the stem and the interlocked nonconducting rings in its other side. This holding element consists of a ring element locked to the inner side of the connecting element by semi-circular movement of the holding element and a spring mechanism that pushes the holding element upwards at the end of the semi-circular movement to avoid spontaneous release. The diameter of the holding element is larger than the diameter of the joined semi flexible rings to enable smooth passage of the joined semi-flexible ring of non-conducting material in its expanded, unfolded configuration, through the connecting apparatus once the holding element is released. Preferred dimensions of the holding element are about 15 mm to 20 mm in diameter. Under the holding element, the inner part of the connecting apparatus is threaded to be screwed to the top of the container that houses the tissue. The leading end of the screw has a serrated shape to match its counter shape at the end of the screwing process therefore irreversibly lock the connecting apparatus to the container. The upper level of the connecting apparatus is connected to the lower level by a thin breakable material located just above the attachment of the holding element with the inner aspect of the connecting apparatus. This double-decker arrangement enables sterile approach to the contained tissue and its holding apparatus in the surgical arena.

The second element, the Injector 250, consists of a small 3 to 5 ml syringe 260 having a modified connecting end. On both sides of the tip at the connecting end there is an exposed electrical contact point adjusted to connect with the contact points of a connecting element to complete an electrical circuit with the heating element 134 that is positioned between the interlocked nonconducting rings 122, 124. Behind the connecting tip of the Injector 250 a switch 256 is positioned. This switch 256 is connected in series with the heating element 134 and may be a push button switch, for example. It is preferably visible and accessible once the Injector 250 is interlocked with the positioner 200.

The syringe 260 of the injector 250 may be filled with air or liquid which may be released via a conduit through the stem 140 and through one or more outlet holes 142 behind the membrane by depressing the plunger of syringe 260 in a typical injecting procedure. Alternatively, instead of introducing fluid via the stem 140, a syringe 260 may be coupled to a separate needle positioned behind the membrane 16.

Embodiments of the invention are thus directed to a tool for removing a section of Descemet's membrane from a donor eye, and for inserting said section into a patient's eye.

In one embodiment, the tool comprises: a distal end consisting of a base ring on a stem; a cover ring for covering the base ring and locking to the base ring by a locking means; a proximal anchor coupled via wires to the base ring, at a distance from the stem, such that applying force to the anchored wires causes the base ring to bend. The tool further comprises a heating element in the base ring, coupled to a power supply via the stem of the tool, such that air or water pressure released from the injector may be used to detach the Descemet's membrane from the stroma in the donor eye and the base ring may be inserted under the Descemet's membrane. The cover ring may then be lowered over the base ring and lockingly engaged with the base ring via the pins or other locking mechanism to securely trap or clasp the Descemet's section between the base ring and the cover ring. The Descemet's section may now be separated from the surrounding eye tissue, using a scalpel or other cutting tool.

Preferably, the distal end of the tool is lockingly insertable into a container of preservation fluid for sealingly storing the section of Descemet's membrane.

To insert into the patient's eye, force is applied to wires anchored to the ring holding the membrane that causing the ring and trapped donor descemet membrane section to flex and curl in a manner analogous to the curling of a sea skate. The curled membrane may be inserted through a short incision in the cornea, as used for extraction of the diseased Descemet's membrane. Once positioned under the hole in the Descemet's membrane, the force on the wires is eased and the rings assume their flat, circular shape. Application of electrical power to the heating element which is a high resistance conductor, burns through the Descemet's membrane releasing the inner disk of Descemet's membrane. Bubbling air or water from the injector under the disk causes it to float up and join the surrounding Descemet's membrane of the patient.

The technique of floating the membrane up using air bubbles is known. The air may be inserted using a separate air pipe or needle. However, in preferred embodiments, the air pipe is integral to the tool of the invention, and the mouth of the air pipe is somewhere central to the base ring or is one or more outlet holes in the base ring.

Thus a tool is described that can be used for both excising a section of Descemet's membrane from a donor eye, and for releasing the section to be floated into position in a recipient patient's eye. The Descemet membrane is manipulated by the edges of the section to be implanted and the section to be implanted is not contacted with knives, hooks and the like, and thus the tissue inserted is suffers less damage than conventional techniques.

The membrane is released by simply burning the tissue at the perimeter of the sample, which is usually circular, detaching the sample from the holder rings.

Preferably the holder with membrane is insertable into a preservation solution and may be stored for a several hours, days or even a few weeks.

FIG. 8 shows a simplified flow diagram of a circuit for providing a controlled pulse of current to the heating element to detach a donor descemet's membrane from the frame.

Figure 10:
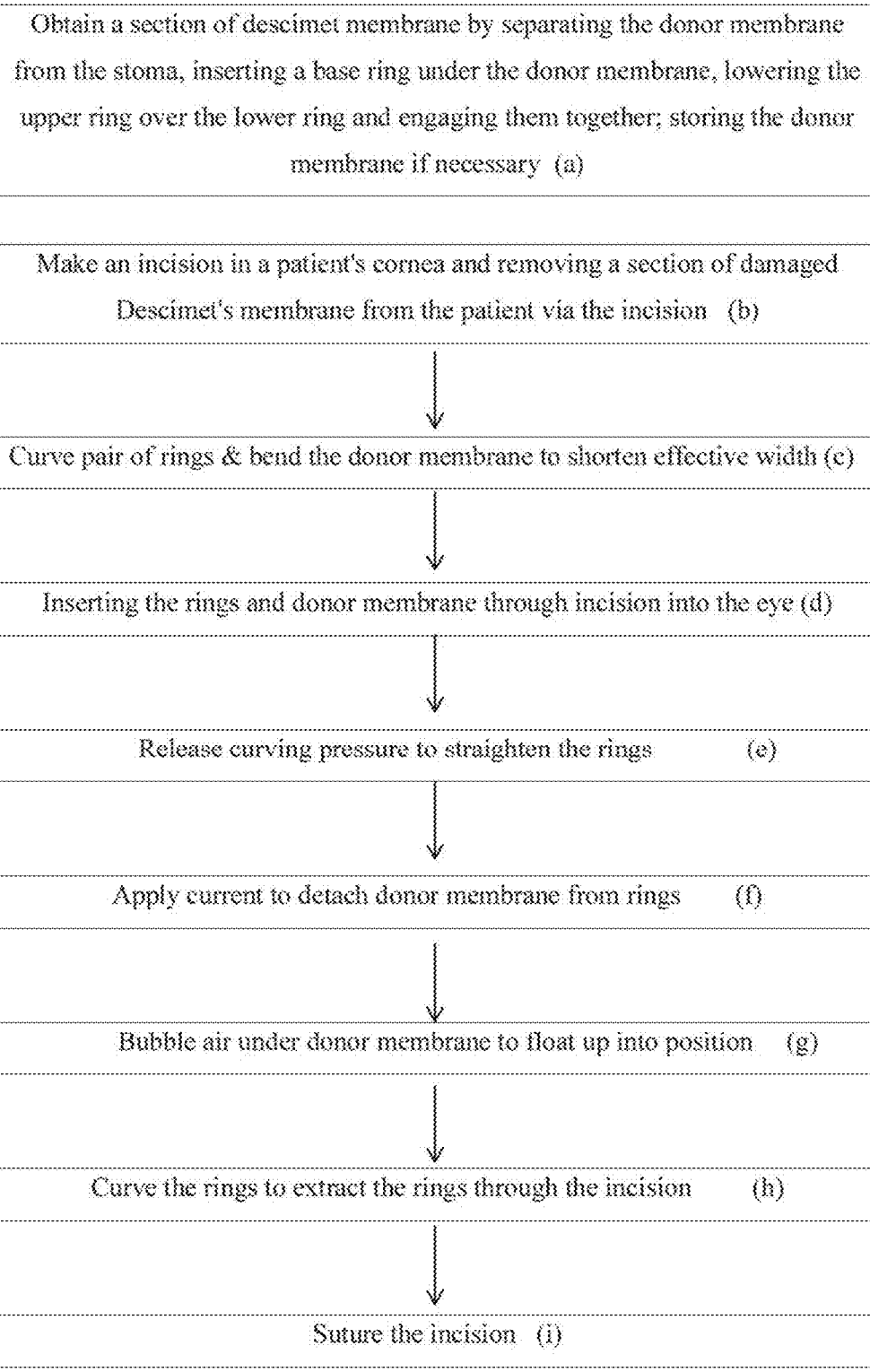
FIG. 10 is a flowchart of steps for performing a Descemet's membrane replacement procedure using the tool of FIG. 6.

With reference to FIG. 10, an aspect of the invention is directed to a method of replacing a Descemet's membrane comprising:

(i) Obtaining a section of Descemet's membrane using the tool of the invention by separating the donor membrane from the stroma, inserting the base ring under the donor membrane, lowering the upper ring over the lower ring and engaging them together; storing the donor membrane if necessary.

(ii) Making incision and removing a damaged Descemet's membrane from a patient via the incision;

(iii) Curving the pair of rings and bending the donor membrane;

(iv) Inserting the rings and donor membrane through incision into the eye;

(v) Releasing curving pressure to straighten the rings;

(vi) Applying current to detach donor membrane from rings;

(vii) Bubbling air under donor membrane to float up into position;

(viii) Curving the rings and extracting through the incision, and (ix) Suturing the incision.

It will be appreciated that the present invention is capable of significant variation. Thus the scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A tool for endothelial manipulation and implantation in a recipient eye, the recipient eye having a cornea, a stoma and an anterior chamber, the tool comprising:
   a) a framework on a stem configured to be insertable through an incision in the recipient eye's cornea between the recipient eye's stoma and the recipient eye's anterior chamber, said framework being positionable to hold a section of Descemet's membrane in a manner suitable for surgical manipulation of said section of Descemet's membrane; and,
   b) a heating element in said framework, said heating element having connecting wires to couple said heating element to a power supply via a switch, said heating element being configured so that activation of the switch burns the perimeter of said section of Descemet's membrane within said framework thereby releasing said section of Descemet's membrane from said framework.

2. The tool of claim 1, wherein said framework is circular.

3. The tool of claim 1, wherein said framework is coupled by the stem to a lid, and said lid being sealingly attachable to a container of solution, and configured so that a section of Descemet's membrane from a donor is sealingly preservable in said solution for a time period.

4. The tool of claim 1, wherein said stem provides fluid communication between at least one outlet in said framework and an injector having a reservoir of gas so that an injection of gas from said injector releases gas below said section of Descemet's membrane to float said section of Descemet's membrane into position against the recipient eye's stoma.

5. A method of surgically replacing a section of Descemet's membrane in a recipient eye, the recipient eye having a cornea, a stoma and an anterior chamber said method comprising the steps of:
   a) obtaining a section of Descemet's membrane from a donor eye, and placing said section of Descemet's membrane on a framework;
   b) making an incision in a recipient eye's cornea and removing a section of damaged Descemet's membrane from the recipient eye via said incision;
   c) inserting said framework containing said section of Descemet's membrane through said incision into said recipient eye to a position between the recipient eye's stoma and the recipient eye's anterior chamber;
   d) applying electrical current to heat the perimeter of said section of Descemet's membrane, thereby detaching said section of Descemet's membrane from said framework, thereby placing said section of Descemet's membrane into an appropriate position in said recipient eye; and
   e) releasing gas below said section of Descemet's membrane to float said section of Descemet's membrane into position against the recipient eye's stoma.

* * * * *